(12) United States Patent
Phillips (10) Patent No.: US 10,058,470 B2
(45) Date of Patent: Aug. 28, 2018

(54) FEMALE URINARY CUP

(71) Applicant: Jerry P. Phillips, Palm Bay, FL (US)

(72) Inventor: Jerry P. Phillips, Palm Bay, FL (US)

( * ) Notice: Subject to any disclaimer, the term of this patent is extended or adjusted under 35 U.S.C. 154(b) by 279 days.

(21) Appl. No.: 14/913,356

(22) PCT Filed: Aug. 20, 2014

(86) PCT No.: PCT/US2014/051960
§ 371 (c)(1),
(2) Date: Feb. 20, 2016

(87) PCT Pub. No.: WO2015/026989
PCT Pub. Date: Feb. 26, 2015

(65) Prior Publication Data
US 2016/0199041 A1  Jul. 14, 2016

Related U.S. Application Data (60) Provisional application No. 61/868,549, filed on Aug. 21, 2013.

(51) Int. Cl.
*A61G 9/00* (2006.01)
*A61B 10/00* (2006.01)
(Continued)

(52) U.S. Cl.
CPC ............ *A61G 9/006* (2013.01); *A61B 10/007* (2013.01); *A61B 10/0045* (2013.01);
(Continued)

(58) Field of Classification Search
CPC .............. A61B 10/007; A61B 10/0096; A61B 10/0045; B65D 25/005; B65D 25/2835
See application file for complete search history.

(56) References Cited

U.S. PATENT DOCUMENTS 3,774,455 A * 11/1973 Seidler ..................... G01N 9/12
422/549
4,221,295 A * 9/1980 Tuchband ............ A61B 10/007
206/564
(Continued)

OTHER PUBLICATIONS

Patent Cooperation Treaty International Search Report for International Application No. PCT/US2014/051960, dated Dec. 8, 2014.
(Continued)

*Primary Examiner* — Devin Henson
(74) *Attorney, Agent, or Firm* — D'Hue Law LLC; Cedric A. D'Hue (57) ABSTRACT

Methods and devices for holding liquid or solid materials including a cylindrical container, a holder, and a detachable handle, the handle capable of being adjusted to variable angles when coupled to the holder. Method of collecting material including the step of holding a graduated cylindrical container by a detachable variable angle handle. A kit for a female urinary cup for holding liquid or solid materials comprising a cylindrical container including exterior threads on which a cap may be screwed, a holder attached to a sidewall of the container, a detachable handle optionally coupled to the holder, the handle capable of being adjusted to variable angles when coupled to the holder, and instructions for use of the female urinary cup.

19 Claims, 6 Drawing Sheets

(51) Int. Cl.
*B65D 25/28* (2006.01)
*B65D 25/00* (2006.01)

(52) U.S. Cl.
CPC ...... *A61B 10/0096* (2013.01); *A61G 2200/12* (2013.01); *B65D 25/005* (2013.01); *B65D 25/2835* (2013.01)

(56) References Cited

U.S. PATENT DOCUMENTS

| | | | |
|---|---|---|---|
| 5,202,094 A | | 4/1993 | Jones et al. |
| D341,421 S | | 11/1993 | Jones |
| D357,066 S | | 4/1995 | Jones et al. |
| 6,485,691 B1 | | 11/2002 | Jones |
| 6,973,678 B2 | | 12/2005 | Jones |
| 7,195,602 B2 | | 3/2007 | Yong et al. |
| 2002/0169395 A1 | | 11/2002 | Huang |
| 2005/0009203 A1* | 1/2005 | Wong ............ | A61B 10/0096 436/518 |
| 2005/0187492 A1* | 8/2005 | Geibel ............ | A61B 10/007 600/573 |
| 2011/0165039 A1* | 7/2011 | Khoury ............ | A61B 10/007 422/547 |

OTHER PUBLICATIONS

Written Opinion of the International Search Authority for International Application No. PCT/US2014/051960, dated Oct. 22, 2014.
Amended Claims for International Application No. PCT/US2014/051960, in reply to the ISR/WO-ISA, dated Dec. 18, 2014.
Letter accompanying amended claims for International Application No. PCT/US2014/051960, in reply to the ISR/WO-ISA, dated Dec. 18, 2014.
International Application No. PCT/US2014/051960, filed Aug. 20, 2014.
GSI Outdoors 79203 Collapsible Green Fairshare Mug. Product listing (online). Amazon.com Sports & Outdoors. Amazon.com. Jul. 24, 2012 (retrieved on Oct. 22, 2014). Retrieved from the internet:<URL:https://web.archive.org/web/20120724022714/http://www.amazon.com/GSI-Outdoors-79203-Collapsible-Fairshare/dp/B002YT4DWQ>.

* cited by examiner

FEMALE URINARY CUP

CROSS TO RELATED APPLICATIONS

This application is a U.S. national phase filing of PCT international patent application serial number PCT/US14/51960, filed Aug. 20, 2014, which claims the benefit of U.S. provisional patent application Ser. No. 61/868,549, filed Aug. 21, 2013, the disclosures of which are expressly incorporated by reference.

FIELD

This disclosure pertains to the field of medical devices, in particular, urinary cups.

BACKGROUND

Collection of a urine specimen can be a cumbersome task. Most often this is due to the design of the specimen collection apparatus. During the collection process patients often unexpectedly soil themselves or do not collect a sufficient amount of urine for testing purposes. Due to anatomy, female patients face additional challenges during urine specimen collection.

Each time a female patient is asked to collect a urine specimen by using the current designed specimen cup she is subjected to getting her hands wet in the collection process. The problem exists whether the collection of urine is taken at home or in a medical facility. This unwelcome situation occurs a majority of the times for all female adults as well as for all female children. Furthermore, adults who assist children in the collection of urine specimens often experience these same issues.

Additionally, the current urine specimen bottles do not have a dual use of collection, mixing and testing in the same receptacle. After collection, transfer of a liquid or solid specimen from the collection bottle to the testing tubes or bottles can also create spills, cause patients or medical personnel to unexpectedly soil themselves, and can increase transfer contamination.

A modification of the collection container design can solve the cumbersome collection process and soiling issues that many individuals experience during collection and transfer for testing.

Several attempts have been made in the field to address the issue and disclose different types of specimen enclosures with fixed handles. For example, U.S. Design Pat. No. D341,421 (R. Shane Jones) shows the ornamental design of a combined wine specimen bottle with a gradient scale, an externally disposed pour spout in the lip of the specimen bottle, a machined-in handle fixedly attached as an extension to the specimen receptacle bottle, and a corresponding cap to cover the specimen bottle and spout. However, the design of the specimen bottle and cap together does not allow for 1) the proper pouring of any liquid samples, 2) ensured sealing of a liquid or solid material sample for mixing or further testing in the receptacle itself, and 3) the ability to detach the handle and process the collected sample without transfer to another testing vehicle.

Additionally, further attempts at addressing the ease and cleanliness of collection have been envisioned with specimen cups and detachable handles. In U.S. Design Pat. No. D357,066 (Timothy B. Jones, et al.), where the ornamental design of a specimen cup and detachable, one-piece handle that is capable of being attached to the cup by a clip socket at a fixed angle for use by the user is taught. Once the handle is attached on top of the clip socket, the handle is immovable until detached. Although this design does attempt to address the need for cleanliness in the collection process, it does not allow the user to adjust to different heights and angles for collection and requires the user to adjust their hand placement on the handle or move their arm to adjust the angle of the cup for collection Also, the dual-chambered, liquid receiving and retaining device of U.S. Pat. No. 7,195,602 (Yong, et al.) comprises a liquid receiving and retaining body, a detachable top cover and a detachable bottom cover for the receiving and retaining body; a funnel-shaped transverse inner wall dividing the receiving and retaining body into an upper liquid receiving and retaining chamber and a lower liquid receiving and retaining chamber; an annular depending locking flange; an orifice stopper disposed in the lower chamber; an annular, spring-like flexible web formed in the bottom cover; and an unattached handle that engages a T-slot element on the receiving and retaining body, that when attached, becomes fixedly permanent. Again, this attachment does not allow a patient user to variable heights or angles and requires the user to adjust their hand positioning on the handle or move their arm to adjust the angle of the receiving and retaining body for collection.

A further example is shown in U.S. Pat. No. 6,973,678 (Timothy B. Jones) where a specimen container and uniform handle are assembled by the patient and used for collection. Here, once the handle is attached to the specimen container, there is no way to adjust the handle to different heights and angles for collection without patient intervention.

Both female and male patients are currently using the same collection cup. Like many medical tools and equipment it appears that no consideration has been given to provide a collection cup that is best suited for females use. Thus, a need remains for ease and cleanliness in the collection process of urine and solid samples and the ability to mix and test the collected samples in the same receptacle.

SUMMARY

The present disclosure includes a urinary cup for holding liquid or solid materials comprising a cylindrical container including exterior threads on which a cap may be screwed, and a holder attached to a sidewall of the container, and a detachable handle optionally coupled to the holder, the handle capable of being adjusted to variable angles when coupled to the holder.

In one embodiment of the urinary cup, the cylindrical container may be graduated. In this embodiment, the cylindrical container includes graduated markings on an external surface of the sidewall.

The sidewall of the cylindrical container defines an inner diameter within the range of approximately 80 millimeters to approximately 100 millimeters, and wherein the sidewall defines an outer diameter of approximately 101 millimeters. The cylindrical container of this embodiment may have an inner diameter of varied length. This varied length is configured to define the depth of a pouring channel. The pouring channel includes a nexus that exists the entire length of the cylindrical container. The inner diameter of the cylindrical container is of maximum length at the nexus of the pouring channel. The nexus of the pouring channel facilitates pouring of contents out of the cylindrical container. The length of the inner diameter varies from approximately 80 millimeters to approximately 110 millimeters.

In this embodiment, the sidewall also defines a pouring channel. The pouring channel decreases the thickness of the sidewall of the container. The pouring channel also exists the entire height of the cylindrical container.

In this embodiment, the holder is attached to the external surface of the sidewall of the cylindrical container in between the open aperture end and the bottom of the container. The handle is coupled to the holder, wherein a female portion of the holder couples to a male portion of the handle.

Further to this embodiment of the specimen cup, the exterior threads are attached to the external sidewall adjacent to the open aperture end of the container.

The present disclosure also includes a method of collecting liquid or solid material comprising the steps of holding a graduated cylindrical container by a detachable variable angle handle under a source of liquid or solid material; and filling the graduated cylindrical container with liquid or solid material from the source. This method can further comprise the step of placing a cap on the graduated cylindrical container; and shaking the container to mix the liquid or solid material within the graduated cylindrical container.

The present disclosure also includes a kit for a female urinary cup for holding liquid and solid materials, comprising a cylindrical container including exterior threads on which a cap may be screwed, a holder attached to a sidewall of the container, a detachable handle optionally coupled to the holder, the handle capable of being adjusted to variable angles when coupled to the holder, and instructions for use of the female urinary cup.

BRIEF DESCRIPTION OF THE DRAWINGS

The above-mentioned and other features of this disclosure, and the manner of attaining them, will become more apparent and the disclosure itself will be better understood by reference to the following description of embodiments of the disclosure taken in conjunction with the accompanying drawings, wherein.

Corresponding reference characters indicate corresponding parts throughout the several views. Although the drawings represent embodiments of the present disclosure, the drawings are not necessarily to scale and certain features may be exaggerated in order to better illustrate and explain the present disclosure.

DETAILED DESCRIPTION OF THE EXEMPLARY EMBODIMENTS

The embodiments disclosed below are not intended to be exhaustive or limit the disclosure to the precise forms disclosed in the following detailed description. Rather, the embodiments are chosen and described so that others skilled in the art may utilize their teachings.

Figure 1A:
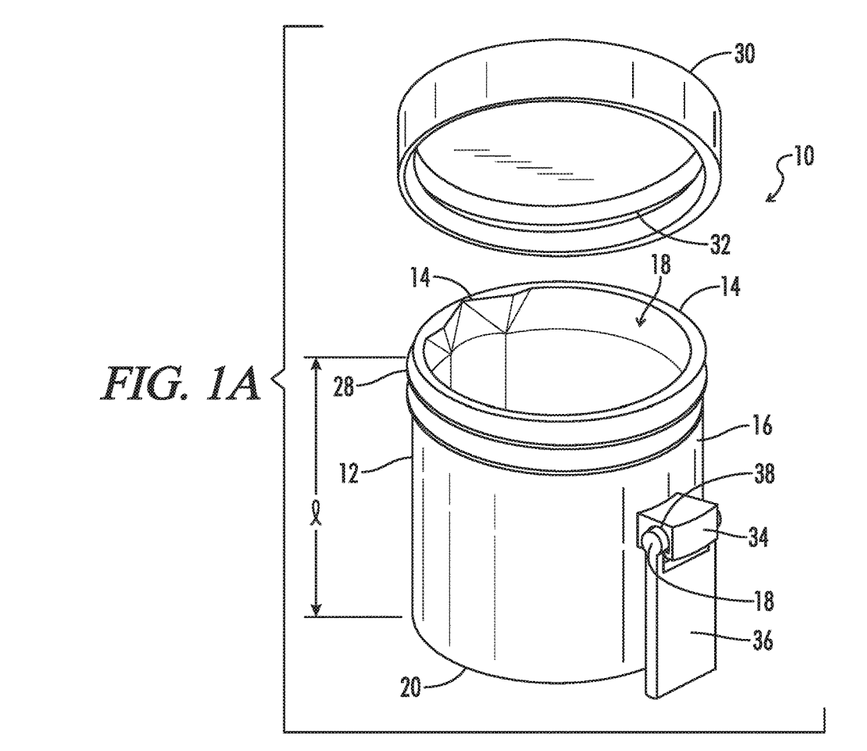
FIG. 1A displays a perspective view of one embodiment of a female urinary cup of the present disclosure.
Figure 1B:
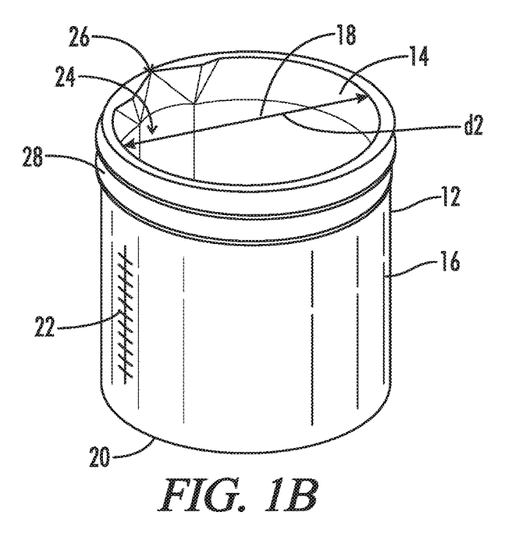
FIG. 1B displays a perspective view of a cylindrical container according to another embodiment of the present disclosure.
Figure 1C:
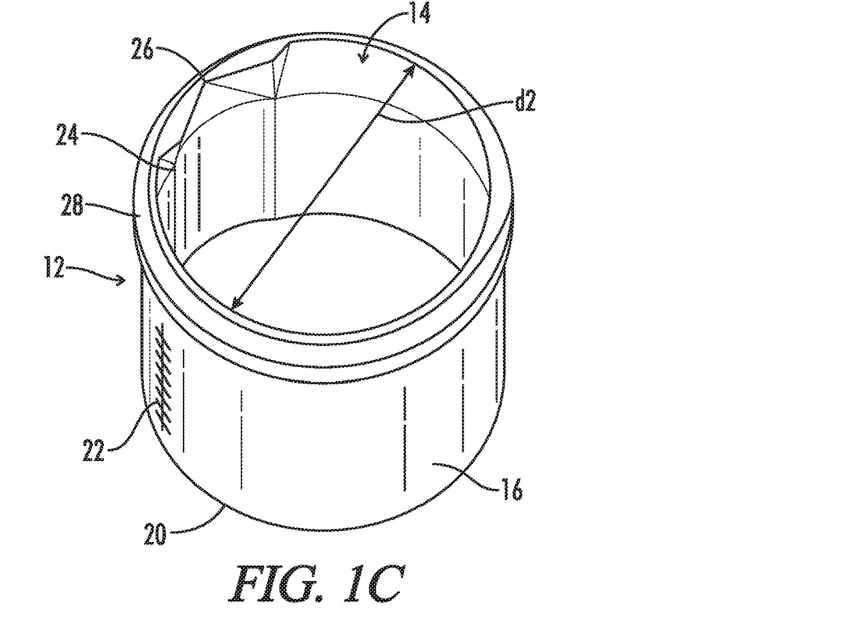
FIG. 1C shows a perspective view of the container of FIG. 1B.
Figure 1D:
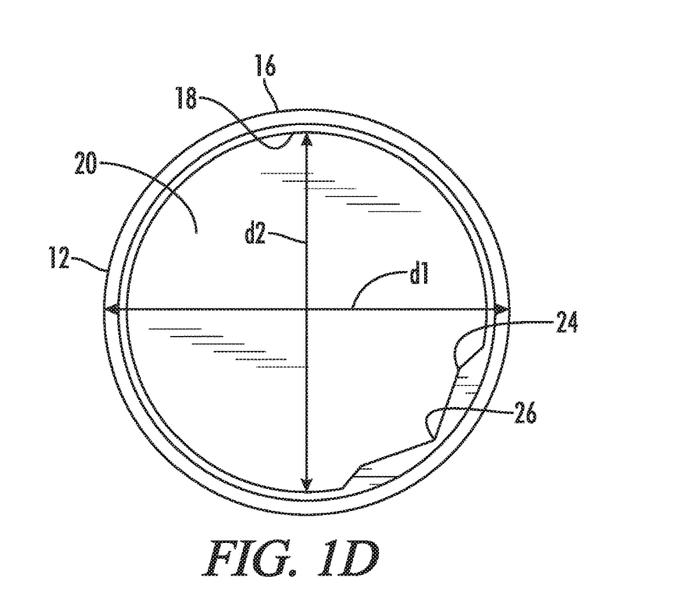
FIG. 1D illustrates a top view of the container of FIG. 1B without a holder.
Figure 2A:
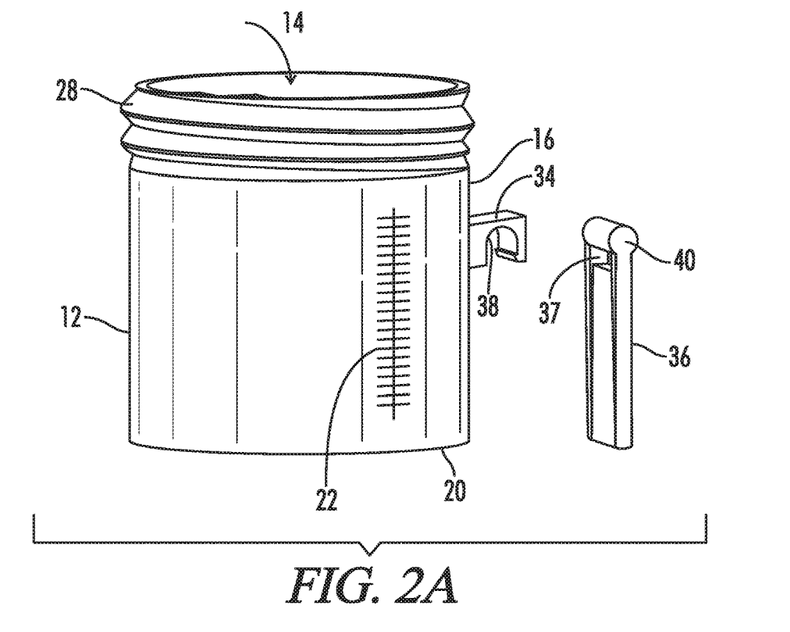
FIG. 2A displays an exploded view of a cylindrical container and handle according to another embodiment of the present disclosure.
Figure 2B:
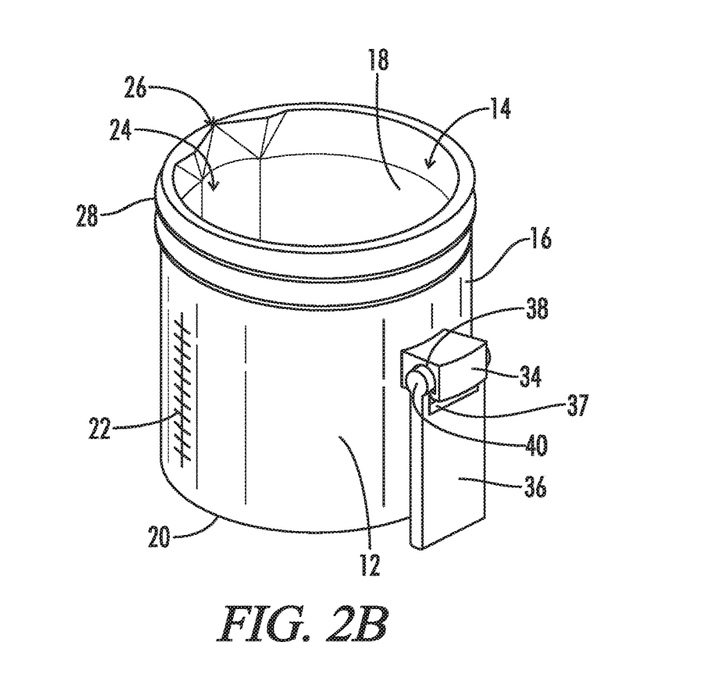
FIG. 2B shows a perspective view of the container of FIG. 2A coupled to the handle of FIG. 2A.
Figure 2C:
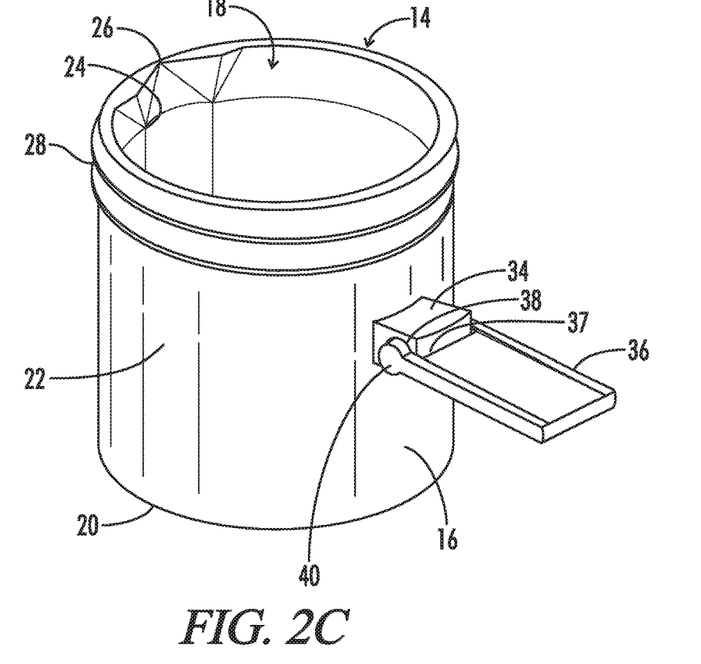
FIG. 2C illustrates another perspective view of the container and handle of FIG. 2A.
Figure 2D:
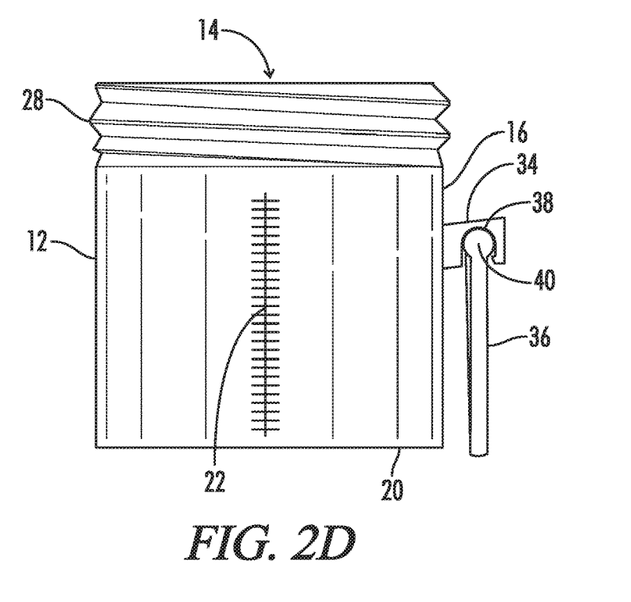
FIG. 2D displays yet another perspective view of the container and handle of FIG. 2A.
Figure 2E:
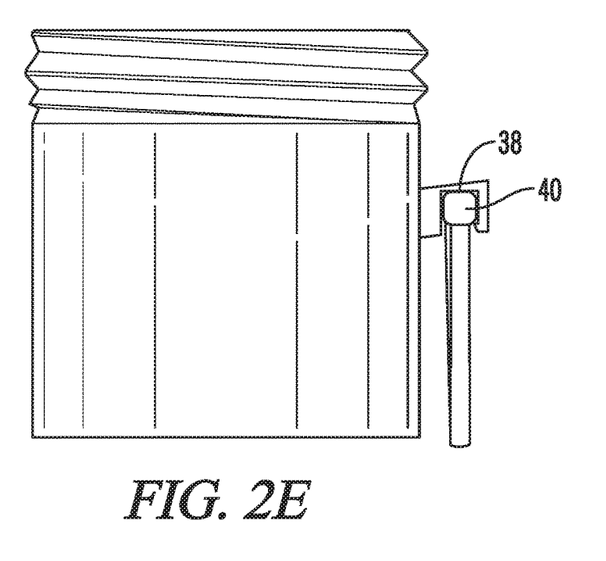
FIG. 2E shows a side view of the container of FIG. 2A and a handle according to another embodiment of the present disclosure.
Figure 2F:
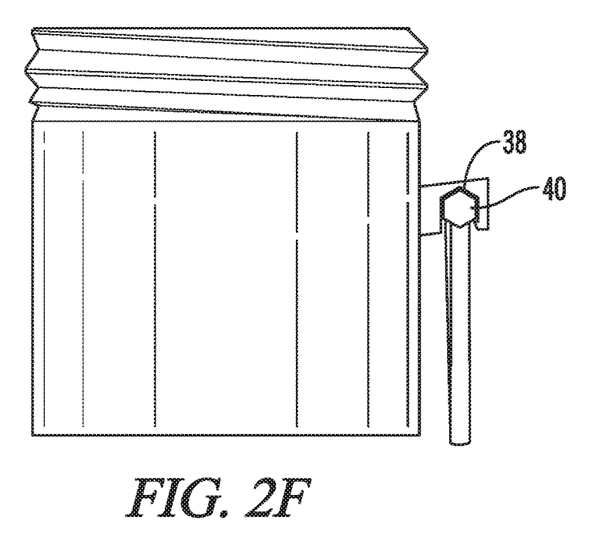
FIG. 2F illustrates a side view of the container of FIG. 2A and a handle according to another embodiment of the present disclosure.

In an embodiment of the present disclosure as illustrated in FIG. 1A, urinary cup 10 for holding liquid or solid materials comprises container 12. Container 12 comprises sidewall 16 defining opening aperture 14 and bottom 20. The sidewall 16 includes exterior threads 28 on which cap 30 may be screwed. Sidewall 16 also supports holder 34. Detachable handle 36 is optionally coupled to holder 34. When coupled to holder 34, handle 36 is capable of being adjusted to variable angles α (FIG. 2d) relative to sidewall 16. Urinary cup 10 can be manufactured out of different materials, including plastics, ceramic, glass, rubber paper and/or cardboard.

Container 12 can be configured to accommodate the differing shapes of the female exterior anatomical structure, and in particularly shaped to cover both the urethral and anal orifices in the vagina and posterior area so that container 12 is capable of being placed in a position that covers most of the vaginal area during collection. This will help eliminate the possibility of a user getting one's hand soiled.

Container 12 includes sidewall 16 which comprises external surface 16 and internal surface 18. Sidewall 16 is configured to define opening aperture 14. Opening aperture 14 is configured to be wide enough to attempt to accommodate female urethral stream issues, such as interaction of the stream with external genital organs of the female anatomy. Container 12 is also configured to be deep enough as not to have specimen overflow issues. Container 12 also has bottom 20, which defines the containing capacity of container 12.

In this embodiment, container 12 is illustrated as generally cylindrical in nature, as shown in FIGS. 1A-1D. Container 12 is envisioned to be conical, rectangular, and other feasible shapes as defined by sidewall 16, opening aperture 14 and bottom 20. Bottom 20 may be a smaller or larger size than opening aperture 14.

Sidewall 16 of cylindrical container 12 may be marked with units to measure volume. Gradient scale 22, as particularly shown in FIGS. 1B, 1C, and 2A-E, may be labeled or etched on sidewall 16 between opening aperture 14 and bottom 20 at a size for standard visibility to the patient user to gauge whether they have collected enough of a urine or solid material specimen. Sidewall 16 defines an outer diameter $d_1$ within the range of about 90 millimeters to about 110 millimeters, and in particular about 96 millimeters when not including exterior threads 28 and about 101 millimeters when including exterior threads 28. External thread 28 is at a thickness within the range of about 2.5 millimeters to about 8 millimeters, in particular about 6 millimeters. Sidewall 16 is at a thickness within the range of about 2 millimeters to about 8 millimeters, in particular about 6 millimeters when not including exterior threads 28 and not including internal pour channel 24. Sidewall 16 defines inner diameter $d_2$ within the range of from about 80 to about 100 millimeters, and in particular about 89 millimeters where not measuring internal pour channel 24 and about 95 millimeters when measuring at internal pour channel 24.

Container 12 defines longitudinal length l within the range from about 100 millimeters to about 110 millimeters, and in particular about 102 millimeters. The length or depth l of container 12 of urinary cup 10 may be varied depending on the specified amount of liquid and solid material that will need to be collected. However, container 12 will be of a sufficient size to accommodate various collection amounts and to be able to fit in a standard commode, water closet, tub, shower or sink.

Sidewall 16 also defines pouring channel 24 to enhance pouring/transferring of a liquid collection to other containers, if necessary, for testing. Pouring channel 24 may be tapered and decreases the thickness of sidewall 16 so that liquid and solid material may be funneled into a stream for transfer. The portion of the sidewall 16 that defines the depth of pouring channel 24 is about 3 millimeters to about 10 millimeters.

Pouring channel 24 also defines nexus 26 that exists longitudinal length l of container 12 to facilitate pouring of liquid or solid materials out of container 12. Inner diameter $d_2$ is at a maximum length at nexus 26 of pouring channel 24, while depth of pouring channel 24 is at a minimum depth within the range of about 4 millimeters to about 8 millimeters, and in particular about 5 millimeters.

In an embodiment of the present disclosure, internal pouring channel 24 extends from bottom 20 to open aperture end 14 of container 12, culminating at a maximum channel depth at nexus 26. In another embodiment of the present disclosure, interior surface of sidewall 16 of container 12 defines pouring channel 24, which includes a depth within the range of about 3 millimeters to about 9 millimeters and extends into the thickness of sidewall 16 of container 12. In other words, sidewall 16 of container 12 may have a uniform thickness or may have a varied thickness to accommodate the desired depth of pouring channel 24. In yet another embodiment, internal pouring channel 24 may have endpoint 26 at open aperture 14 of container 12.

Once liquid or solid material specimen is collected in container 12, internal pouring channel 24 directs the flow of the specimen out of container 12 into other containers for testing, if required. However, urinary cup 10 is capable of mixing specimen, storing specimen and using specimen for testing without transfer. An advantage of having internal pouring channel 24 is that container 12 can also have threads on the external surface of container 12. Sidewall 16 of container 12 may include exterior threads 28 adjacent to open aperture end 14 for effective sealing of screw cap 30. Screw cap 30 includes interior threads 32 which are matching, paired and/or sister onto container 12. Providing cap 30 can also be accomplished in other embodiments, such as, a snug fit cap instead of a screw cap with threads.

External sidewall 16 also supports holder 34 machined in or fixedly attached to the external surface of sidewall 16. Holder 34 may be located anywhere between open aperture end 14 and bottom 20 of container 12. Holder 34 may be located within the range of about 50 millimeters to about 80 millimeters, in particular about 63.5 millimeters from bottom 20. Holder 34 may be of any typical known fastening device in this industry, including but not limited to a clip, latch-key, key and lock, or hinge fastening device capable of allowing its connecting detachable handle 36 to couple and rotate about the holder connection at varying angles α. Angles α include any angle relative to sidewall 16 within the range of about 0° to about 180°. Exemplary angles α include about 70°, 90°, and 110°.

Detachable varying angle handle 36 may be optionally removed and discarded or reused to couple to reusable container 12 if desired. Handle 36 is capable of extending from about 8 inches to about 10 inches from container 12. Handle 36 can be any length, width or thickness. In one embodiment, handle 36 is about 75 millimeters long, about 23 millimeters wide and about 3 millimeters thick.

The design and shape of handle 36 is for ease of handling and collection of the urine while avoiding getting a patient user's hand wet. Handle 34 design makes holding and maneuvering container 12 possible during specimen collection. In a particular embodiment, handle 36 is a unitary solid piece. In another particular embodiment, handle 36 is formed of multiple pieces. Handle 36 is of a length, width and thickness less than the internal dimensions of external sidewall 16 of disclosed container 12 so that handle 36 may be stored in container 12 and cap 30. Storage of handle 36 is beneficial when cup 10 is being shipped or not in use.

In one embodiment, as shown in FIGS. 1A and 2A-2F, holder 34 has groove 38 for detachable coupling to corresponding abutment 40 of handle 36. As handle 36 is optional, handle 36 is removable from urinary cup 10. When attached handle 36 can detent into a plurality of predetermined angles relative to specimen cup 10. Specifically, groove 38 and abutment 40 may each comprise matching cross sections defining any number of regular convex polygonal shapes, such as triangle, square (See FIG. 2E), pentagon, hexagon (See FIG. 2F), heptagon, octagon, etc. It is envisioned that the shapes are not necessarily equilateral but may be provided to include beneficial predetermined angles relative to specimen cup 10.

In one particular embodiment of the present disclosure, holder 34 is a clip that is permanently attached to external sidewall 16 of container 12. In another embodiment of the present disclosure, handle 36 includes a solid arm piece. In another embodiment, handle 36 defines aperture 37 for receipt of a portion of holder 34. In yet another embodiment of the present disclosure, as shown in FIG. 1A, handle 36 also includes male portion couple 40 that is movably placed in female portion 38 of holder 34. In still yet another embodiment of the present disclosure, handle 36 includes a female portion that is movably placed on a male portion of holder 34.

In another embodiment of the present disclosure, a method of collecting liquid or solid material comprises the step of holding graduated cylindrical container 12 by detachable variable angle handle 36 under a stream of liquid or solid material or a patient user's urethral or anal orifices and filling graduated cylindrical container 12 with liquid or solid material from the stream. Once filled, cap 30 may be placed on opening aperture end 14 of container 12 and the sample may be shaken for homogeneous mixing of the collected sample, may be transported, may be transferred, or may be directly tested in urinary cup 10.

Figure 3:
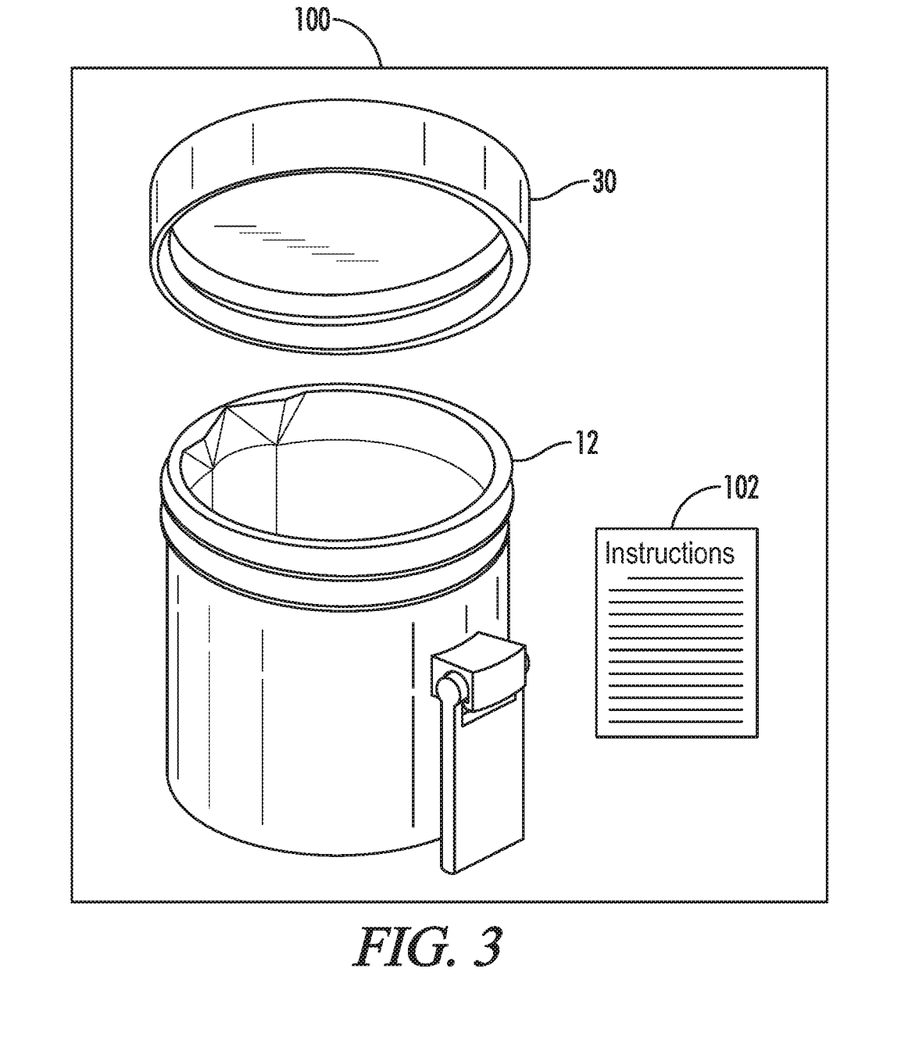
FIG. 3 illustrates a perspective view of an embodiment of a female urinary cup kit.

In another embodiment of the present disclosure, specimen collection kit 100 for urinary cup 10 of the present disclosure comprises container 12, screw cap 30 and variable angle detachable handle 36. If male patients find it accommodating not to use handle 36 they may choose not to use handle 36 by not coupling handle 36 to container 12 or by coupling handle 36 adjacent to sidewall 16 of container 12, or discarding handle 36. If an individual patient user decides to attach handle 36, handle 36 can be attached to container 12 at a number of angles α relative to external sidewall 16 of container 12. It is envisioned that the number of angles may comprise discreet angles or a gradient.

The device of this disclosure is not limited to the collection of urine or liquids. There are several practical uses, such as kitchen applications, for this type of container. The container can be used to collect any type of volumetric measurable material i.e. liquids or solids. Depending on the actual use of container 12, variable angled handle 36 can be attached or detached. A benefit of container 12 is the option of attaching screw cap 30 included in kit 100 for easy mixing of material within container 12. Internal pouring channel 24 does not distort external threads 28 of side walls 16 of cylindrical container 12. Internal pouring channel 24 allows for external threads for attaching screw cap 30 to container 12. Side walls 16 may or may not include a spout. Lack of a spout also aids in a securely fitting top.

Once female urinary cup 10 or its individual parts is/are manufactured, kit 100 may be packaged with detachable variable angle handle 36 inside of container 12 and screw cap 30 coupled to container 12 alongside instructions for use 102. This configuration of kit 100 will allow the end user the option to attach handle 36 if needed for their particular use or discard handle 36.

While this disclosure has been described as having an exemplary design, the present disclosure may be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains.

What is claimed is:

1. A urinary cup for holding liquid or solid materials comprising:
    a cylindrical container including exterior threads on which a cap may be screwed,
    a holder attached to a sidewall of the container, and
    a handle coupled to the holder, wherein a coupling is formed by a male portion in the handle and a female portion in the holder, wherein a cross section of the coupling defines a polygon, wherein the handle can detent into a plurality of predetermined angles when coupled to the holder, wherein the plurality of predetermined angles is defined by the polygon, and wherein the handle is detachable from the holder.

2. The cup of claim 1 wherein the sidewall defines an inner diameter within a range of approximately 80 millimeters to approximately 100 millimeters, wherein the sidewall defines an outer diameter of approximately 101 millimeters.

3. The cup of claim 2 wherein the inner diameter is of varied length.

4. The cup of claim 3 wherein the varied length is configured to define a depth of a pouring channel.

5. The urinary cup of claim 1, wherein the polygon is selected from 3 to 8 sides.

6. The urinary can of claim 1, wherein the plurality of predetermined angles is comprised of 70°, 90°, and 110°.

7. The urinary cup of claim 1, wherein the polygon is not equilateral.

8. A urinary cup for holding liquid or solid materials comprising:
    a cylindrical container including a sidewall, the sidewall defining an internal pouring channel that exists a longitudinal length of the cylindrical container,
    the sidewall including exterior threads on which a cap may be screwed,
    a handle, and
    a holder attached to the sidewall of the container,
    wherein the internal pouring channel is of a maximum depth at a nexus of the pouring channel and wherein the nexus exists along the longitudinal length of the container,
    wherein a coupling is formed by a male portion in the handle and a female portion in the holder, wherein a cross section of the coupling defines a polygon,
    wherein the handle can detent into plurality of predetermined angles when coupled to the holder, and wherein the plurality of predetermined angles is defined by the polygon.

9. The cup of claim 8 wherein the inner diameter of the container is at a maximum length at the nexus.

10. The cup of claim 9 wherein the nexus facilitates pouring of contents out of the container.

11. The cup of claim 8 wherein a horizontal length of the inner diameter of the cylindrical container varies from approximately 100 millimeters to approximately 110 millimeters.

12. The cup of claim 8 wherein the pouring channel increases a thickness of the sidewall of the container.

13. The cup of claim 8 wherein the pouring channel decreases a thickness of the sidewall of the container.

14. The cup of claim 8 wherein the pouring channel exists the entire longitudinal length of the cylindrical container.

15. The cup of claim 8 wherein the holder is attached to the sidewall in between an open aperture end and a bottom of the container.

16. The cup of claim 8 wherein the exterior threads are attached to the sidewall adjacent to an open aperture end of the container.

17. A method of collecting liquid or solid material comprising the step of:
    holding a device comprising:
    a cylindrical container including, exterior threads on which a cap may be screwed,
    a holder attached to a sidewall of the container, and
    a handle coupled to the holder, wherein a coupling is formed by a male portion in the handle and a female portion in the holder, wherein a cross section of the coupling defines a polygon, wherein the handle can detent into plurality of predetermined angles when coupled to the holder, wherein the plurality of predetermined angles is defined by the polygon, and wherein the handle is detachable from the holder;
    and
    filling the device with liquid or solid material from the source.

18. The method of claim 17 further comprising the steps of:
    placing a cap on the device; and
    shaking the container to mix material within the device.

19. A kit for a female urinary cup for holding liquid or solid materials comprising:
    a device comprising:
    a cylindrical container including exterior threads on which a cap may be screwed,
    a holder attached to a sidewall of the container, and
    a handle coupled to the holder, wherein a coupling is formed by a male portion in the handle and a female portion in the holder, wherein a cross section of the coupling defines a polygon, wherein the handle can detent into plurality of predetermined angles when coupled to the holder, wherein the plurality of predetermined angles is defined by the polygon, and wherein the handle is detachable from the holder, and
    instructions for use of the female urinary cup.

* * * * *